United States Patent [19]

Williams

[11] Patent Number: 5,030,633

[45] Date of Patent: Jul. 9, 1991

[54] USE OF ANDROSTANE DERIVATIVE AGAINST MALIGNANT HYPERTHERMIA

[76] Inventor: Charles H. Williams, 200 Shadow Mountain #75, El Paso, Tex. 79912

[21] Appl. No.: 581,834

[22] Filed: Sep. 12, 1990

[51] Int. Cl.$^5$ .......................................... A61K 31/535
[52] U.S. Cl. .................................................. 514/231.5
[58] Field of Search ..................................... 514/231.5

Primary Examiner—Stanley J. Friedman
Attorney, Agent, or Firm—William M. Blackstone

[57] ABSTRACT

The use of an androstane derivative of the formula

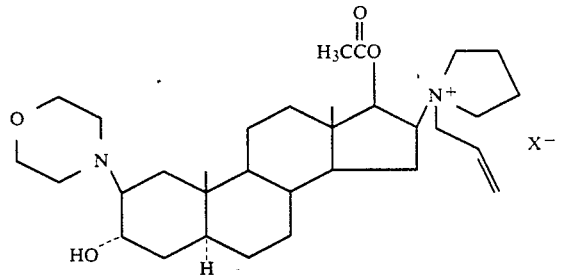

in which X$^-$ represents a pharmaceutically acceptable anion, or its pharmaceutically acceptable salts for the preparation of a medicament with prophylactic properties against malignant hyperthermia.

1 Claim, No Drawings

USE OF ANDROSTANE DERIVATIVE AGAINST MALIGNANT HYPERTHERMIA

The present invention concerns the use of an androstane derivative of the formula

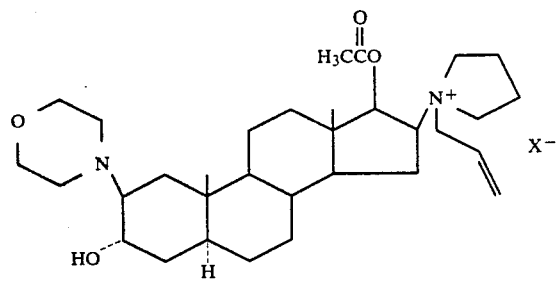

in which $X^-$ represents a pharmaceutically acceptable anion, or its pharmaceutically acceptable salts for the preparation of a medicament with prophylactic properties against malignant hyperthermia. Said androstane derivative I is known from European patent application No. 0,287,150, in which this compound has been described as a useful neuromuscular blocking agent. It has now been found that the androstane derivative I also exhibits very valuable prophylactic properties against malignant hyperthermia (MH). MH is a rare myogenic hypermetabolic syndrome that is associated with certain commonly used anaesthetic agents and muscle relaxants. Its incidence is reported to be about 1:50,000, but if triggered MH often appears to be lethal. The combination succinylcholine-halothane is notorious as an MH trigger, and for MH-suseptible (MHS) patients up to now dantrolene is the drug of choice for use as MH prophylaxis.

The role of neuromuscular blocking agents in triggering the MH syndrome is highly disputed. Although some reports state that neuromuscular blockers do not trigger the MH syndrome, others report cases of MH in which such compounds are the probable triggering agent. Short [Anest. Analg., 55, 643-653 (1976)] and Hall [Br. J. Anaest., 48, 1135-1141 (1976)], for instance, reported that pancuronium does not inititate the syndrome in swine. Short reported that pnacuronium prevents the syndrome in response to succinylcholine administration. Hall studied the effects of d-tubocurarine and pancuronium on both succinylcholine and halothane induced MH. While d-tubocurarine prevented the hyperpyrexia secondary to succinylcholine, it did not prevent the syndrome in response to halothane. Following pretreatment with pancuronium only half their MHS pigs survived exposure to halothane. Hoech et al [in: Thermoregulatory Mechanisms and their Terapeutic Implications, 4th International Symposium on the Pharmacology of Thermoregulation, Oxford, 1979, pp 137-141 (Karger, Basel 1980)] showed that metubine iodode would prevent the development of MH in 19 of 22 MHS pigs. Buzello [Anest. Analg., 64, 515-519 (1985)] tried to use vecuronium to abort the MH syndrome and was not successful. Although the possibility has been discussed regularly, in fact there is no experimental evidence to suggest that neuromuscular blocking agents would be useful in treating the full blown MH syndrome.

Surprisingly, this invention clearly demonstrates that androstane derivative I has a significant effect on preventing MH by blocking the development of MH through a neurogenic mechanism even though the muscle twitch has returned to normal values. Androstane derivative I cause a marked decrease in core temperature and in rectal temperature. During halothane and succinylcholine administration a decrease of core temperature of about 0.5° C. was observed, whereas a final core temperature decrease of about 1.2° C. was obtained. Rectal temperature showed a similar decrease with an initial temperature drop of about 0.5° C. to a final temperature decrease of about 1.1° C. MSH or control animals treated with vecuronium or arduan did not exhibit these significant changes in core and rectal temperature. Most remarkably, the androstane derivative I is not only able to decrease the core and rectal temperature during its infusion, but more inportantly, the carryover effect at the end of the infusion period and after exposure of the patient to halothane for 30 min (even though full muscle twitch had been recovered) prevented the depolarizing effect of succinylcholine and thereby preventing the triggering of MH. In contrast, challenge of the arduan treated MSH patient in the same time frame with halothane and succinylcholine resulted in the full blown MH syndrome in all patients. This property, therefore, makes androstane derivative I pre-eminently suitable as a prophylactic drug for treating MH.

The pharmaceutically acceptable anion and salt, may be derived from organic or anorganic acids such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, ascorbic acid, etc. The bromide is the preferred anion and hydrobromic acid the preferred acid addition salt.

By means of pharmaceutically suitable liquids the compound I can be applied as an injection preparation in the form of a solution, suspension or emulsion or as a spray, e.g. a nasal spray. For humans the daily dosage is preferably 0.01-50 mg per kg body weight.

The invention is illustrated by the following example.

EXAMPLE

Ten MHS pigs (wt. 50.93 kg) and eight control pigs (wt. 53.55 kg) were used. Thiopental (22 mg/kg) was given for sedation. The animal was intubated and mechanically ventilated. Surgical cutdowns were completed to the external jugular vein and carotid artery. An Opticath catheter was threaded to the wedge position in the pulmonary artery. A Millar Mikro-Tip pressure transducer catheter was retrograde threaded to the left ventricle. End tidal $CO_2$ was monitored with the Milwaukee Electronics 7050 Series Capnograph. A Grass FT transducer, HSE neuromuscular monitor, and HSE neurostimulator set at supramaximal (TO4) (0.2 ms, 2 Hz, 15 sec) was used to stimulate the left peroneal nerve and record the twitch response. The measured and calculated parameters were a.o. the core and the rectal temperature.

Result:

| Compound I | | | | |
|---|---|---|---|---|
| CORE TEMPERATURE CONTROL | | | | |
| Sample 1 Cont-1 | Sample 2 Cont-2 | Sample 3 Cont 90-1 | Sample 4 Cont 90-2 | Sample 5 Alk-1 |
| 1 38.12 | 38.00 | 38.02 | 38.28 | 38.34 |
| 2 37.86 | 38.14 | 37.48 | 37.60 | 37.68 |

Compound I (continued)

| | | | | | |
|---|---|---|---|---|---|
| 3 | 38.00 | 38.01 | 37.96 | 38.02 | 38.06 |
| 4 | 37.99 | 37.92 | 37.90 | 37.92 | 37.65 |
| 5 | 38.53 | 38.51 | 37.45 | 37.35 | 37.27 |
| 6 | 38.53 | 38.54 | 38.04 | 38.06 | 38.24 |
| 7 | 38.69 | 38.40 | 38.20 | 38.15 | 37.90 |
| 8 | 38.25 | 38.29 | 38.27 | 38.30 | 38.28 |

| | Sample 6 Alk-2 | Sample 7 Acid-1 | Sample 8 Acid-2 | Sample 9 Hal. | Sample 10 Succ. |
|---|---|---|---|---|---|
| 1 | 38.43 | 38.75 | 38.82 | | |
| 2 | 37.70 | 38.10 | 38.17 | 37.60 | |
| 3 | 38.08 | 38.22 | 38.34 | 38.54 | 38.68 |
| 4 | 37.52 | 38.06 | 38.04 | 38.01 | 37.91 |
| 5 | 37.33 | 37.52 | 37.77 | 37.62 | 37.43 |
| 6 | 37.73 | 38.56 | 38.70 | 38.43 | 38.26 |
| 7 | 37.36 | 38.03 | 38.11 | 37.63 | 37.67 |
| 8 | 38.32 | 38.81 | 38.95 | 38.28 | 38.17 |
| No. | 8 | 8 | 8 | 8 | 8 |
| MEAN | 38.24 | 38.26 | 37.92 | 37.96 | 37.93 |
| SDEV | 0.31 | 0.31 | 0.30 | 0.33 | 0.37 |
| MIN | 37.86 | 37.92 | 37.45 | 37.35 | 37.27 |
| MAX | 38.69 | 38.84 | 38.27 | 38.30 | 38.34 |
| No. | 8 | 8 | 8 | 7 | 6 |
| MEAN | 37.83 | 38.26 | 38.36 | 38.02 | 38.02 |
| SDEV | 0.40 | 0.43 | 0.42 | 0.41 | 0.45 |
| MIN | 37.33 | 37.52 | 37.77 | 37.60 | 37.43 |
| MAX | 38.43 | 38.81 | 38.95 | 38.54 | 38.68 |

MH

| | Sample 1 Cont-1 | Sample 2 Cont-2 | Sample 3 Cont 90-1 | Sample 4 Cont 90-2 | Sample 5 Alk-1 |
|---|---|---|---|---|---|
| 1 | 38.06 | 37.99 | 37.55 | 37.59 | 37.41 |
| 2 | 36.91 | 36.76 | 36.21 | 36.08 | 35.88 |
| 3 | 37.30 | 37.27 | 36.89 | 36.83 | 36.68 |
| 4 | 36.41 | 36.60 | 36.83 | 36.75 | 36.65 |
| 5 | 37.40 | 37.39 | 36.97 | 36.92 | 36.37 |
| 6 | 36.74 | 36.72 | 35.77 | 35.62 | 35.49 |
| 7 | 38.00 | 37.80 | 37.97 | 38.01 | 38.03 |
| 8 | 38.00 | 38.03 | 37.82 | 37.80 | 37.74 |
| 9 | 37.57 | 37.24 | 36.65 | 36.60 | 36.17 |
| 10 | 36.81 | 36.74 | 36.85 | 36.85 | 36.88 |

| | Sample 6 Alk-2 | Sample 7 Acid-1 | Sample 8 Acid-2 | Sample 9 Hal. | Sample 10 Succ. |
|---|---|---|---|---|---|
| 1 | 37.64 | 37.41 | 37.36 | 35.94 | 35.39 |
| 2 | 35.66 | 35.66 | 35.56 | 34.63 | 34.47 |
| 3 | 36.62 | 36.76 | | 36.22 | 36.03 |
| 4 | 36.50 | 36.77 | 36.90 | 35.83 | 35.64 |
| 5 | 36.26 | 36.52 | 36.49 | 36.02 | 35.82 |
| 6 | 35.42 | 35.55 | 35.60 | 34.95 | 34.88 |
| 7 | 38.00 | 38.29 | 38.33 | 37.60 | 38.44 |
| 8 | 37.73 | 37.95 | 38.12 | 37.22 | 36.85 |
| 9 | 36.03 | 36.51 | 36.56 | 35.72 | 35.72 |
| 10 | 36.89 | 36.96 | 36.96 | 37.60 | 36.98 |
| No. | 10 | 10 | 10 | 10 | 10 |
| MEAN | 37.32 | 37.24 | 36.95 | 36.91 | 36.73 |
| SDEV | 0.59 | 0.54 | 0.68 | 0.74 | 0.81 |
| MIN | 36.41 | 36.60 | 35.77 | 35.62 | 35.49 |
| MAX | 38.06 | 38.03 | 37.97 | 38.01 | 38.03 |
| No. | 10 | 10 | 9 | 10 | 10 |
| MEAN | 36.68 | 36.84 | 36.88 | 36.17 | 36.02 |
| SDEV | 0.89 | 0.88 | 0.97 | 1.03 | 1.15 |
| MIN | 35.42 | 35.55 | 35.56 | 34.63 | 34.47 |
| MAX | 38.00 | 38.29 | 38.33 | 37.60 | 38.44 |

CHALLENGE

| | Sample 1 Cont-1 | Sample 2 Cont-2 | Sample 3 Hal | Sample 4 Succ. 1 | Sample 5 Succ. 2 | Sample 6 Succ. 3 |
|---|---|---|---|---|---|---|
| 2 | 37.45 | | | 37.02 | 37.06 | |
| 3 | 37.51 | | | 37.59 | 37.50 | 38.11 |
| 4 | 37.45 | 37.39 | 37.12 | | | |
| 5 | 36.56 | 36.19 | 35.14 | 34.74 | | |
| 6 | 37.95 | 37.68 | 37.12 | 36.53 | 37.00 | 37.03 |
| 8 | 37.96 | 37.93 | 37.01 | 36.51 | | |
| 10 | 37.91 | 37.54 | 37.06 | | | |
| No. | 7 | 5 | 7 | 5 | 2 | 1 |
| MEAN | 37.58 | 37.35 | 36.87 | 36.47 | 37.56 | 37.03 |
| SDEV | 0.50 | 0.65 | 0.79 | 1.05 | 0.78 | |
| MIN | 36.56 | 36.19 | 33.14 | 34.74 | 37.00 | 37.03 |
| MAX | 37.96 | 37.93 | 37.59 | 37.50 | 38.11 | 37.03 |

Cont-1 = control period 10 min.
Cont-2 = control period 30 min.
Cont 90-1 = comp. I infusion 20 min.
Cont 90-2 = comp. I infusion 40 min.
Alk-1 = alkalosis 10 min.
Alk-2 = alkalosis 30 min.
Acid-1 = acidosis 10 min.
Acid-2 = acidosis 30 min.
Hal = halothane exposure 2% for 30 min.
Succ = succinylcholine exposure (2 mg/kg)
Succ-1 = succinylcholine exposure 10 min.
Succ-2 = succinylcholine exposure 20 min.
Succ-3 = succinylcholine exposure 30 min.

Compound I

RECTAL TEMPERATURE CONTROL

| | Sample 1 Cont-1 | Sample 2 Cont-2 | Sample 3 Cont 90-1 | Sample 4 Cont 90-2 | Sample 5 Alk-1 |
|---|---|---|---|---|---|
| 1 | 38.4 | 38.3 | 38.0 | 38.3 | 38.5 |
| 2 | 38.2 | 37.5 | 36.9 | 36.6 | 36.6 |
| 3 | 38.3 | 38.2 | 38.0 | 38.0 | 38.0 |
| 4 | 38.4 | 38.5 | 37.9 | 37.9 | 37.7 |
| 5 | 37.5 | 37.5 | 35.2 | 35.0 | 35.0 |
| 6 | 38.7 | 39.0 | 38.2 | 38.2 | 38.3 |
| 7 | 39.1 | 38.9 | 38.3 | 38.2 | 38.1 |
| 8 | 37.9 | 37.8 | 37.0 | 36.6 | 36.3 |

| | Sample 6 Alk-2 | Sample 7 Acid-1 | Sample 8 Acid-2 | Sample 9 Hal. | Sample 10 Succ. |
|---|---|---|---|---|---|
| 1 | 38.5 | 38.6 | 38.9 | | |
| 2 | 36.5 | 36.2 | 36.4 | 36.2 | |
| 3 | 38.0 | 38.0 | 38.1 | 38.3 | 38.3 |
| 4 | 37.7 | 37.8 | 37.9 | 38.0 | 37.9 |
| 5 | 34.7 | 34.9 | 35.2 | 34.8 | 35.0 |
| 6 | 38.4 | 38.5 | 38.6 | 38.6 | 38.4 |
| 7 | 37.9 | 37.8 | 38.0 | 37.8 | 37.6 |
| 8 | 36.2 | 36.0 | 36.0 | 36.0 | 36.0 |
| No. | 8 | 8 | 8 | 8 | 8 |
| MEAN | 38.3 | 38.2 | 37.4 | 37.3 | 37.3 |
| SDEV | 0.5 | 0.6 | 1.0 | 1.2 | 1.2 |
| MIN | 37.5 | 37.5 | 35.2 | 35.0 | 35.0 |
| MAX | 39.1 | 39.0 | 38.3 | 38.3 | 38.5 |
| No. | 8 | 8 | 8 | 7 | 6 |
| MEAN | 37.2 | 37.2 | 37.4 | 37.1 | 37.2 |
| SDEV | 1.3 | 1.3 | 1.3 | 1.4 | 1.4 |
| MIN | 34.7 | 34.9 | 35.2 | 34.8 | 35.0 |
| MAX | 38.5 | 38.6 | 38.9 | 38.6 | 38.4 |

MH

| | Sample 1 Cont-1 | Sample 2 Cont-2 | Sample 3 Cont 90-1 | Sample 4 Cont 90-2 | Sample 5 Alk-1 |
|---|---|---|---|---|---|
| 1 | 37.8 | 37.7 | 37.2 | 37.1 | 37.0 |
| 2 | 36.4 | 36.4 | 35.7 | 35.6 | 35.5 |
| 3 | 37.4 | 37.4 | 36.9 | 36.9 | 36.6 |
| 4 | 36.6 | 36.6 | 36.8 | 36.8 | 36.7 |
| 5 | 37.7 | 37.5 | 37.2 | 37.2 | 37.0 |
| 6 | 36.5 | 36.9 | 35.5 | 35.5 | 35.5 |
| 7 | 38.5 | 38.2 | 38.2 | 38.2 | 38.3 |
| 8 | 37.5 | 37.3 | 37.0 | 37.0 | 36.8 |
| 9 | 37.2 | 37.2 | 36.7 | 36.6 | 36.5 |
| 10 | 37.2 | 37.2 | 37.3 | 37.2 | 37.3 |

| | Sample 6 Alk-2 | Sample 7 Acid-1 | Sample 8 Acid-2 | Sample 9 Hal. | Sample 10 Succ. |
|---|---|---|---|---|---|
| 1 | 36.9 | 36.7 | 36.7 | 36.2 | 35.7 |

Compound I -continued

| | | | | | |
|---|---|---|---|---|---|
| 2 | 35.3 | 35.1 | 35.1 | 34.3 | 34.2 |
| 3 | 36.6 | 36.6 | | 36.4 | 36.2 |
| 4 | 36.6 | 36.5 | 37.0 | 36.5 | 36.5 |
| 5 | 36.8 | 36.8 | 36.7 | 36.5 | 36.4 |
| 6 | 35.5 | 35.2 | 35.2 | 35.0 | 35.1 |
| 7 | 38.3 | 38.5 | 38.3 | 38.5 | 38.5 |
| 8 | 36.8 | 37.2 | 37.0 | 36.5 | 36.5 |
| 9 | 36.2 | 36.4 | 36.5 | 36.3 | 36.0 |
| 10 | 37.2 | 37.4 | 37.4 | 37.5 | 37.4 |
| No. | 10 | 10 | 10 | 10 | 10 |
| MEAN | 37.3 | 37.2 | 36.8 | 36.8 | 36.7 |
| SDEV | 0.7 | 0.5 | 0.8 | 0.8 | 0.8 |
| MIN | 36.4 | 36.4 | 35.5 | 35.5 | 35.5 |
| MAX | 38.5 | 38.2 | 38.2 | 38.2 | 38.3 |
| No. | 10 | 10 | 9 | 10 | 10 |
| MEAN | 36.6 | 36.6 | 36.7 | 36.4 | 36.2 |
| SDEV | 0.8 | 1.0 | 1.0 | 1.2 | 1.2 |
| MIN | 35.5 | 35.1 | 35.1 | 34.3 | 34.2 |
| MAX | 38.3 | 38.5 | 38.3 | 38.5 | 38.5 |

CHALLENGE

| | Sample 1 Cont-1 | Sample 2 Cont-2 | Sample 3 Hal | Sample 4 Succ. 1 | Sample 5 Succ. 2 | Sample 6 Succ. 3 |
|---|---|---|---|---|---|---|
| 2 | 37.0 | | 37.0 | 37.0 | | |
| 3 | 38.4 | | 38.5 | 38.4 | 38.6 | |
| 4 | 37.7 | 37.7 | 37.4 | | | |
| 5 | 36.0 | 35.7 | 35.9 | 35.2 | | |
| 6 | 38.5 | 38.0 | 37.7 | 37.5 | 37.4 | 37.5 |
| 8 | 37.5 | 37.5 | 37.0 | 36.0 | | |
| 10 | 38.5 | 38.1 | 37.9 | | | |
| No. | 7 | 5 | 7 | 5 | 2 | 1 |
| MEAN | 37.7 | 37.4 | 37.3 | 36.8 | 38.0 | 37.50 |
| SDEV | 0.9 | 1.0 | 0.8 | 1.3 | 0.9 | |
| MIN. | 36.0 | 35.7 | 35.9 | 35.2 | 37.4 | 37.5 |
| MAX. | 38.5 | 38.1 | 38.4 | 38.6 | 38.4 | 37.5 |

VECURONIUM
CORE TEMPERATURE MH Pigs

| | Sample 1 | Sample 2 | Sample 3 | Sample 4 |
|---|---|---|---|---|
| 1. | 39.60 | 39.90 | 40.00 | 40.00 |
| 2. | 40.30 | 40.60 | 40.90 | 40.90 |
| 3. | 39.70 | 40.40 | 40.80 | 40.90 |
| 4. | 41.70 | 42.00 | 44.90 | 45.60 |
| 5. | 41.40 | 42.00 | 43.60 | 45.30 |
| 6. | 39.20 | 39.50 | 39.60 | 39.60 |
| 7. | 37.60 | 37.90 | 38.00 | 38.20 |
| 8. | 39.70 | 39.80 | 39.90 | 39.90 |

| | Sample 5 | Sample 6 | Sample 7 |
|---|---|---|---|
| 1. | 39.50 | 39.50 | 39.50 |
| 2. | 40.90 | 40.70 | 40.70 |
| 3. | 41.30 | | 42.10 |
| 4. | | | |
| 5. | | | |
| 6. | 41.20 | 42.50 | 42.10 |
| 7. | 38.20 | 38.60 | 38.50 |
| 8. | 40.10 | 40.10 | 40.10 |
| No. | 8 | 8 | 8 | 8 | 6 | 5 | 6 |

VECURONIUM -continued

| | | | | | | | |
|---|---|---|---|---|---|---|---|
| MEAN | 39.90 | 40.26 | 40.96 | 41.30 | 40.22 | 40.28 | 40.50 |
| SDEV | 1.29 | 1.35 | 2.24 | 2.70 | 1.19 | 1.46 | 1.44 |
| MIN | 37.60 | 37.90 | 38.00 | 38.20 | 38.20 | 38.50 | 38.50 |
| MAX | 41.70 | 42.00 | 44.90 | 45.60 | 41.30 | 42.50 | 42.10 |

RECTAL TEMPERATURE MH Pigs

| | Sample 1 | Sample 2 | Sample 3 | Sample 4 |
|---|---|---|---|---|
| 1. | 39.30 | 39.90 | 40.00 | 40.00 |
| 2. | 40.10 | 40.40 | 40.80 | 40.80 |
| 3. | 39.80 | 40.30 | 40.60 | 40.80 |
| 4. | 41.50 | 41.80 | 44.80 | 45.80 |
| 5. | 41.30 | 41.80 | 43.20 | 44.80 |
| 6. | 39.30 | 39.80 | 39.80 | 39.80 |
| 7. | 37.50 | 37.80 | 37.90 | 38.00 |
| 8. | 39.80 | 39.90 | 40.00 | 40.00 |

| | Sample 5 | Sample 6 | Sample 7 |
|---|---|---|---|
| 1. | 39.90 | 39.80 | 39.80 |
| 2. | 40.50 | 40.20 | 42.60 |
| 3. | 41.10 | | 41.33 |
| 4. | | | |
| 5. | | | |
| 6. | 40.80 | 41.50 | 43.20 |
| 7. | 38.20 | 38.90 | 43.50 |
| 8. | 40.10 | 40.20 | 43.80 |
| No. | 8 | 8 | 8 | 8 | 6 | 5 | 6 |
| MEAN | 39.83 | 40.21 | 40.89 | 41.25 | 40.10 | 40.12 | 42.37 |
| SDEV | 1.25 | 1.27 | 2.15 | 2.66 | 1.03 | 0.94 | 1.53 |
| MIN | 37.50 | 37.80 | 37.90 | 38.00 | 38.20 | 38.90 | 39.80 |
| MAX | 41.50 | 41.80 | 44.80 | 45.80 | 41.10 | 41.50 | 43.80 |

Sample 1 = Vecuronium infusion (time = 0).
Sample 2 = Vecuronium infusion (time = 30).
Sample 3 = Vecuronium infusion (time = 45).
Sample 4 = Vecuronium infusion (time = 60 min).
Sample 5 = Vecuronium + Halothane (time = 15 min).
Sample 6 = Vecuronium + Halothane (time = 30 min).
Sample 7 = Final Temperature.

The results of the arduan infusion for one hour in seven MHS pigs and eight control pigs demonstrate that arduan did not have any significant effect on core or rectal temperature.

I claim:

1. A method for preventing malignant hyperthermia in a patient treated with an anaesthetic agent or a muscle relaxant comprising administering to said patient an effective amount of an androstane derivative of the formula

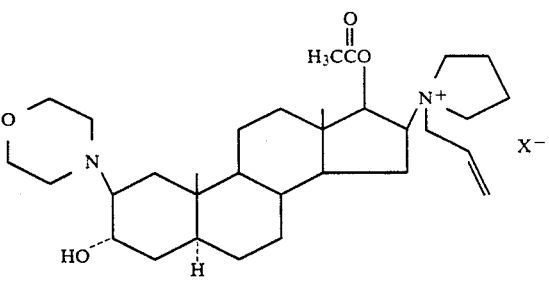

in which x⁻ represents a pharmaceutically acceptable anion, or the pharmaceutically acceptable salts of said androstane derivative.

* * * * *